United States Patent [19]

Iimuro et al.

[11] Patent Number: 4,798,654

[45] Date of Patent: Jan. 17, 1989

[54] PROCESS FOR PREPARING BISPHENOL A

[75] Inventors: Shigeru Iimuro; Takashi Kitamura, both of Nagoya; Yoshio Morimoto, Tokai, all of Japan

[73] Assignee: Mitsui Toatsu Chemicals, Inc., Tokyo, Japan

[21] Appl. No.: 184,181

[22] Filed: Apr. 21, 1988

[30] Foreign Application Priority Data

May 6, 1987 [JP] Japan .................. 62-108964

[51] Int. Cl.$^4$ .................. B01D 3/10; C07C 37/74
[52] U.S. Cl. .................. 203/94; 203/98; 203/DIG. 9; 568/724
[58] Field of Search .............. 203/48, 94, 98, DIG. 9; 568/724; 202/176

[56] References Cited

U.S. PATENT DOCUMENTS

| | | | |
|---|---|---|---|
| 2,791,616 | 5/1957 | Luton, Jr. | 568/724 |
| 3,290,390 | 12/1966 | Prahl et al. | 568/724 |
| 3,365,375 | 1/1968 | Nixon, Jr. | 203/98 |
| 4,158,611 | 6/1979 | Cooke | 203/80 |
| 4,160,110 | 7/1979 | Carnahan, Jr. | 203/6 |
| 4,192,955 | 3/1980 | Reinitz | 568/724 |
| 4,294,994 | 10/1981 | Li | 568/724 |
| 4,333,801 | 6/1982 | Pajado | 203/94 |
| 4,354,046 | 10/1982 | Ladewig et al. | 568/724 |
| 4,374,283 | 2/1983 | Aneja | 568/724 |
| 4,400,553 | 8/1983 | Aneja | 568/724 |
| 4,447,655 | 5/1984 | Mendiratta | 568/724 |
| 4,469,561 | 9/1984 | Sikdar et al. | 203/39 |
| 4,492,807 | 1/1985 | Aneja | 568/724 |

FOREIGN PATENT DOCUMENTS

| | | | |
|---|---|---|---|
| 36-23335 | 12/1961 | Japan . | |
| 45-22539 | 7/1970 | Japan . | |
| 45-39251 | 12/1970 | Japan . | |
| 50-12428 | 5/1975 | Japan . | |
| 51-91240 | 8/1976 | Japan . | |
| 52-42790 | 10/1977 | Japan . | |
| 56-1297 | 1/1981 | Japan . | |
| 56-13700 | 3/1981 | Japan . | |
| 8003464 | 1/1982 | Netherlands | 203/94 |
| 0991307 | 5/1965 | United Kingdom | 568/724 |
| 1010824 | 11/1965 | United Kingdom | 568/724 |
| 1377227 | 12/1974 | United Kingdom | 568/724 |

Primary Examiner—David L. Lacey
Assistant Examiner—V. Manoharan
Attorney, Agent, or Firm—Burns, Doane, Swecker & Mathis

[57] ABSTRACT

This invention relates to a process for preparing 2,2-bis(4-hydroxyphenyl)propane, e.g. bisphenol A and particularly to a process for preparing high quality bisphenol A with good workability by distilling the intermediate adduct of bisphenol A and phenol.

The adduct of bisphenol A and phenol is fed to a distillation column. Phenol is recovered from the top of the column and bisphenol A is obtained from its bottom. In this distillation process, the adduct of bisphenol A and phenol is added with a part of recycled bottom liquid. Consequently troubles such as plugging of the distillation column are prevented, continuous operation becomes possible for a long period of time and high quality bisphenol A can be steadily obtained.

9 Claims, 1 Drawing Sheet

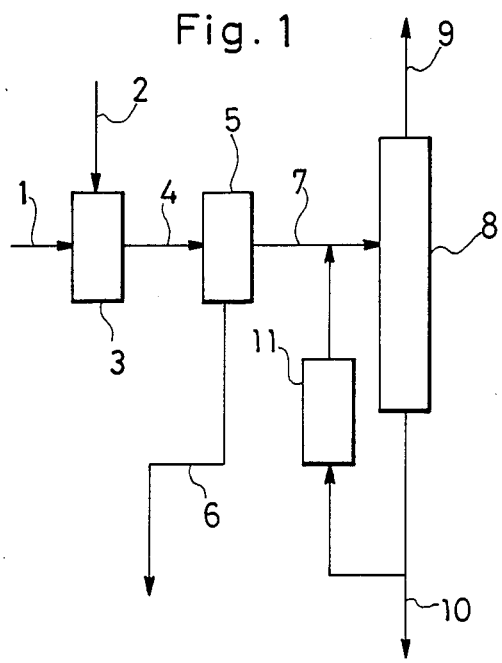
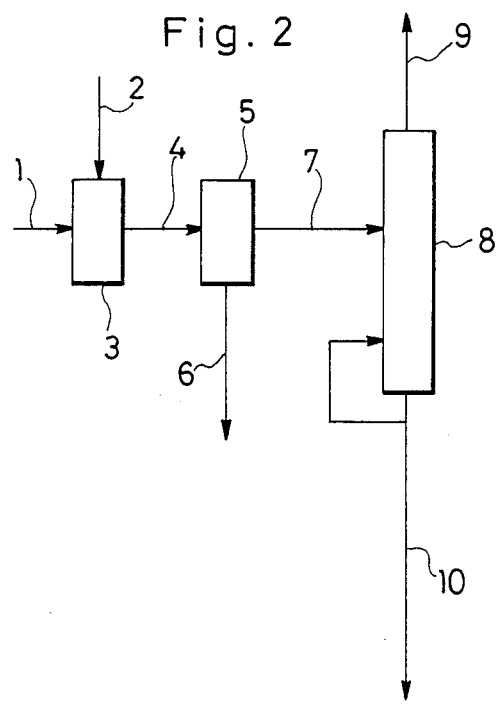

PROCESS FOR PREPARING BISPHENOL A

BACKGROUND OF THE INVENTION

The present invention relates to a process for preparing high purity 2,2-bis(4-hydroxyphenyl)propane (hereinafter referred to as bisphenol A).

Bisphenol A is used as a raw material for polycarbonate resins or epoxy resins, and colorless and high purity bisphenol A is required for polycarbonate resin in particular.

Bisphenol A is prepared from acetone and excess phenol in the presence of an acidic catalyst, in some cases by the addition of an auxiliary catalyst such as sulfur compounds. The reaction mixture contains the catalyst, unreacted acetone, unreacted phenol, water formed by the reaction and other by-products of the reaction.

The by-products are mainly composed of 2-(2-hydroxyphenyl)2-(4-hydroxyphenyl)propane and also contain Dianin's compound, trisphenol, polyphenol and undesirable colored substances. These by-products deteriorate the properties of resin prepared from bisphenol A.

In a process for recovering high purity bisphenol A from the reaction mixture, the catalyst, water and a small amount of phenol are removed from the reaction mixture. The residual liquid mixture is cooled to crystallize the adduct of bisphenol A and phenol. The crystals are separated from the mother liquor containing the by-products of the reaction and then bisphenol A is recovered by removing phenol from the adduct.

As a process for removing phenol from the adduct of bisphenol A and phenol, various methods such as distillation, extraction, steam stripping etc. have been proposed.

For example, Japanese Patent Publication TOKKOSHO No. 52-42790 (1977) discloses a process for vaporizing the adduct at above 180° C. for 0.1–30 minutes under reduced pressure and then obtaining bisphenol A by fractional condensation.

Japanese Patent Publication TOKKOSHO 36-23335 (1961) teaches a process for heating the adduct at 50° C. or more by use of a solvent having a boiling point of at least 50° C. and dissolving the phenol part alone in the solvent.

A distillation process is generally used because it is carried out with simple equipment and without other solvents or water. For example, Japanese Patent Publication TOKKOSHO No. 56-13700 (1981) describes a process for distilling off phenol under reduced pressure, then removing the decomposable low-boiling fractions by a fore-running removal column and successively obtaining bisphenol A by distillation. In addition, there are disclosed processes for obtaining bisphenol A, after removing phenol under reduced pressure, by conducting the distillation in the presence of stabilizers such as aliphatic dicarboxylic acid esters [Japanese Patent Publication TOKKOSHO No. 45-22539 (1970)], glycols [Japanese Patent Publication TOKKOSHO 45-3925 (1970)] and propylene glycol or epoxy resin [Japanese Patent Publication TOKKOSHO No. 56-1297 (1981)].

In the process of distilling the adduct of bisphenol A and phenol and obtaining phenol from the top of column and bisphenol A from the bottom respectively, adduct crystals or their fused liquid are required to be heated above a specific temperature prior to being fed into the distillation column. High temperatures are required for completely eliminating phenol. For example, Japanese Patent Publication TOKKOSHO No. 50-12428 (1975) teaches that desirable heating temperatures are at least 205° C., e.g. the temperature at which phenol crystals are subjected to stripping.

The present inventors have found that bisphenol A solidifies in the distillation column and finally the operation becomes impossible when the temperature of adduct crystals or their fused liquid which are fed to the distillation column is lower than a specific temperature. Therefore the inventors have extensively investigated in order to overcome the above problem. Consequently, when the operating pressure is at least 50 Torr, it has been found that to prevent the solidification, the fused liquid of the adduct is fed to the distillation column at not less than 120° C. or the bottom temperature of the column is maintained at not less than 180° C. Under these conditions, however, substantial amounts of phenol remain so as to yield only substantially useless bisphenol A. On the other hand, when the operating pressure is less than 50 Torr, the solidification can be prevented by maintaining the temperature of the feed not less than 205° C. Besides a column having a diameter of several centimeters such as used in the laboratory can be continuously operated by external heating, even though the feeding temperature or the bottom temperature is outside of above mentioned range. The external heating of the column, however, has been found not to be practical for industrial scale equipment.

On the other hand, treatment of bisphenol A at too high a temperature causes undesirable decomposition and the intact bisphenol A obtained from the bottom of column has been found useless as a product even though any of above process is employed.

SUMMARY OF THE INVENTION

The object of this invention is to provide a process for removing phenol from the adduct of bisphenol A and phenol without exposing bisphenol A to temperatures higher than needed.

BRIEF DESCRIPTION OF THE DRAWINGS

FIG. 1 is a flow diagram illustrating an embodiment of the process of this invention for removing phenol.

FIG. 2 is a flow diagram illustrating an embodiment of the process outside of this invention for removing phenol.

DETAILED DESCRIPTION OF THE INVENTION

The inventors have extensively investigated in order to achieve the above stated objects. Consequently it has been found that, in the process of a distilling off phenol from the top of a distillation column and recovering 2,2-bis(4-hydroxyphenyl)propane from its bottom, recycling of a part of the bottom liquid enables an efficient removal of phenol and a continuous operation of the distillation column for a long period of time. Thus, the objects of the present invention have been achieved.

That is, the present invention is a process for preparing 2,2-bis(4-hydroxyphenyl)propane comprising:

(a) feeding an adduct of 2,2-bis(4-hydroxyphenyl)propane and phenol in the form of crystals, a fused liquid or a mixture thereof to a distillation column;

(b) distilling the adduct and removing phenol from the top of the distillation column and a stream containing 2,2-bis(4-hydroxyphenyl)propane from the bottom of the distillation column; and (c) recycling a portion of the stream containing 2,2-bis(4-hydroxyphenyl)propane removed from the bottom of the distillation column and combining said portion with the adduct being fed to the distillation column.

The adduct of phenol and bisphenol A which is used as the raw material of this invention includes, for example, the adduct directly obtained from the reaction product, adduct crystals prepared by concentrating the filtrate after removing the separated adduct from the reaction mixture, and furthermore crystals obtained by recrystallizing a mixture of crude bisphenol A and phenol.

Such adduct can be prepared, for example, by conducting a condensation reaction of phenol and acetone in the presence of a hydrochloric acid catalyst, distilling off hydrochloric acid, water and a small amount of phenol from the reaction product and cooling the residual mass. Besides the adduct can also be provided by directly cooling the effluent from a fixed bed reactor packed with cation exchange resin. Furthermore, as disclosed in Japanese Laid-Open Patent TOKKAISHO No. 51-91240 (1976), the adduct can also be crystallized by adding water to a mixture of bisphenol A and phenol prior to cooling.

According to the process of this invention, any type of distillation column such as a packed column or a plate column may be used for removing phenol. External heating is not needed so long as heat loss is avoided. When both components are simultaneously fed to the column in the process of this invention, they may be mixed prior to or directly after entering into the column.

The recycled liquid is desired to be heated in order to supply the heat quantity required for evaporating phenol from the adduct.

According to the process of this invention, the distillation column can be operated at an internal liquid temperature in the range of 160°-200° C. and under pressure in the range of 10-100 Torr.

Bisphenol A obtained after removing phenol may be used as a product as it is or after further subjecting it to purification or forming in other steps.

The process of this invention will be illustrated by way of diagrams. FIG. 1 is a flow diagram illustrating an embodiment of the process for removing phenol according to the process of this invention.

In the process of this invention, the mixture (1) consisting of bisphenol A, phenol and impurities is cooled in a crystallizing vessel (3) with the addition of water (2) to crystallize the adduct of bisphenol A and phenol.

In the next step, the slurry (4) of the adduct is charged in a separator (5) to separate the adduct (7) from mother liquor (6). The adduct (7) is fed to a dephenolation column (8). Phenol (9) is removed from the top of column and bisphenol A (10) containing a small amount of phenol is obtained from the bottom of the column.

A part of bisphenol A (10) is recycled through a heater (11) according to the process of this invention and a part of the remaining portion is taken out and transferred to the next step.

In addition, in order to more clearly illustrate the process of this invention, FIG. 2 illustrates a conventional embodiment for separating phenol. In FIG. 2, the numbers 1–10 mean the same as in FIG. 1.

According to the process of this invention, phenol can easily be removed from the adduct of bisphenol A and phenol. Additionally, the dephenolation column can be operated continuously for a long period of time according to the process of this invention. Good quality products can be obtained in accordance with this invention without exposing bisphenol A to unnecessarily high temperatures.

EXAMPLES

This invention will hereinafter be illustrated in detail in respect to example and comparative example.

EXAMPLE 1

In FIG. 1, a mixture (1) consisting of bisphenol A, phenol and impurities was charged into a crystallizing vessel (3) at the rate of 400 kg/hour and at the same time water (2) was added at the rate of 50 kg/hour. The resulting slurry (4) of the adduct of bisphenol A and phenol was charged into a separator (5) to separate the adduct (7) from mother liquor (6). The adduct (6) was heated to 120° C., fused and fed at the rate of 160 kg/hour to a dephenolation column (8) having an internal diameter of 30 cm. A part of the bottom liquid in the dephenolation column was heated to 190° C. in a heater (11) and fed to the column together with the adduct (7). Phenol (9) was mostly removed at 15 Torr, 170° C. and bisphenol A (10) which was taken out of the bottom of column had a phenol content of 2% or less. No plugging of the column has occurred and a stable operation has continued for a year.

COMPARATIVE EXAMPLE 1

In FIG. 2, the same fused liquid of the adduct (7) as in Example 1 was fed to the dephenolation column respectively at 150° C., 180° C. and 210° C. Bisphenol A (10), however, was not recycled according to the process of this invention, but circulated within the bottom only. Crystals were observed to gradually grow from the position below the feed location and the column was plugged to stop the operation respectively after 2 hours, 5 hours and 12 hours.

What is claimed is:

1. A process for preparing 2,2-bis(4-hydroxyphenyl)-propane comprising:
    (a) feeding an adduct of 2,2-bis(4-hydroxyphenyl)-propane and phenol to a distillation column a;
    (b) distilling the adduct and removing phenol from the top of the distillation column and a stream containing 2,2-bis(4-hydroxyphenyl)propane from the bottom of the distillation column; and
    (c) recycling a portion of the stream containing 2,2-bis(4-hydroxyphenyl)propane removed from the bottom of the distillation column and combining said portion with the adduct being fed to the distillation column.

2. The process of claim 1 wherein said portion is combined with the adduct prior to being fed into the distillation column.

3. The process of claim 1 wherein said portion is fed to the distillation column and combined with the adduct directly thereafter.

4. The process of claim 1 wherein said portion is heated prior to being combined with the adduct.

5. The process of claim 1 wherein the distillation column is a packed column.

6. The process of claim 1 wherein the distillation column is a plate column.

7. The process of claim 1 wherein the stream containing 2,2-bis(4-hydroxyphenol)propane removed from the bottom of the distillation column contains less than 2% by weight of phenol.

8. The process of claim 1 wherein the adduct is fed to the distillation column in the form of crystals.

9. The process of claim 1 wherein the adduct is fed to the distillation column in the form of a fused liquid.

* * * * *

UNITED STATES PATENT AND TRADEMARK OFFICE
CERTIFICATE OF CORRECTION

PATENT NO. : 4,798,654
DATED : January 17, 1989
INVENTOR(S) : Shigeru IIMURO, Takashi KITAMURA and Yoshio MORIMOTO It is certified that error appears in the above-identified patent and that said Letters Patent is hereby corrected as shown below:

IN THE CLAIMS:

In claim 1, line 47, delete "a", second occurrence, and insert -- operated at a temperature of from 160°C to 200°C and at a pressure of from 10 to 100 torr --.

Signed and Sealed this

Twentieth Day of June, 1989

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,798,654
DATED      : January 17, 1989
INVENTOR(S): SHIGERU IIMURO et al It is certified that error appears in the above-identified patent and that said Letters Patent is hereby corrected as shown below:

In claim 7, line 2, amend "hydroxyphenol" to -- hydroxyphenyl --.

Signed and Sealed this

Twenty-ninth Day of August, 1989

*Attest:*

DONALD J. QUIGG

*Attesting Officer*  *Commissioner of Patents and Trademarks*